(12) United States Patent
Strand et al.

(10) Patent No.: US 12,713,530 B2
(45) Date of Patent: Aug. 18, 2026

(54) FULLY PRINTED SENSOR WITH INTERNAL ION RESERVOIRS

(71) Applicant: THE REGENTS OF THE UNIVERSITY OF COLORADO, Denver, CO (US)

(72) Inventors: Elliot J. Strand, Boulder, CO (US); Eloise Bihar, Boulder, CO (US); Gregory L. Whiting, Boulder, CO (US)

(73) Assignee: The Regents of the University of Colorado, Denver, CO (US)

( * ) Notice: Subject to any disclaimer, the term of this patent is extended or adjusted under 35 U.S.C. 154(b) by 120 days.

(21) Appl. No.: 18/571,984

(22) PCT Filed: Jun. 21, 2022

(86) PCT No.: PCT/US2022/034394
§ 371 (c)(1),
(2) Date: Dec. 19, 2023

(87) PCT Pub. No.: WO2022/271739
PCT Pub. Date: Dec. 29, 2022

(65) Prior Publication Data

US 2024/0237206 A1 Jul. 11, 2024

Related U.S. Application Data

(60) Provisional application No. 63/330,187, filed on Apr. 12, 2022, provisional application No. 63/213,500, filed on Jun. 22, 2021.

(51) Int. Cl.
*H05K 1/09* (2006.01)
*C09D 11/037* (2014.01)
(Continued)

(52) U.S. Cl.
CPC .......... *H05K 1/092* (2013.01); *C09D 11/037* (2013.01); *C09D 11/102* (2013.01); *C09D 11/52* (2013.01);
(Continued)

(58) Field of Classification Search
CPC .. H05K 1/092; H05K 3/12; H05K 2201/0329; H05K 2201/10151; H05K 2203/122
See application file for complete search history.

(56) References Cited

U.S. PATENT DOCUMENTS 4,225,410 A 9/1980 Pace
5,634,835 A 6/1997 Wu et al.
(Continued)

FOREIGN PATENT DOCUMENTS

WO 2020/132679 A1 6/2020

OTHER PUBLICATIONS

International Search Report and Written Opinion received for PCT Patent Application No. PCT/US2022/034394, mailed on Oct. 19, 2022, 11 pages.
(Continued)

*Primary Examiner* — Nathan Milakovich
(74) *Attorney, Agent, or Firm* — Workman Nydegger

(57) ABSTRACT

A printed electric circuit comprises a printed planar substrate. The printed planar surface comprises one or more traces integrated into the printed planar structure. The one or more traces comprise a hydrophilic additive to create ion reservoirs within an organic semiconductor layer.

15 Claims, 4 Drawing Sheets

(51) Int. Cl.

| | |
|---|---|
| ***C09D 11/102*** | (2014.01) |
| ***C09D 11/52*** | (2014.01) |
| ***G01N 33/00*** | (2006.01) |
| ***H05K 1/11*** | (2006.01) |
| ***H05K 3/12*** | (2006.01) |

(52) U.S. Cl.

CPC ............... *H05K 1/111* (2013.01); *H05K 3/12* (2013.01); *G01N 33/0098* (2013.01)

(56) References Cited

U.S. PATENT DOCUMENTS

| | | | |
|---|---|---|---|
| 2013/0040154 A1 | 2/2013 | Bentley et al. | |
| 2016/0116427 A1* | 4/2016 | Laurenson | B05D 5/00 427/2.13 |
| 2016/0126417 A1 | 5/2016 | Ray et al. | |
| 2017/0315078 A1 | 11/2017 | Laurenson | |
| 2017/0325724 A1 | 11/2017 | Wang et al. | |
| 2018/0066132 A1 | 3/2018 | Nair et al. | |
| 2018/0325244 A1 | 11/2018 | Jeong et al. | |
| 2019/0131555 A1* | 5/2019 | Doris | H10K 19/10 |
| 2019/0293595 A1* | 9/2019 | Walsh | G01N 27/308 |
| 2020/0027847 A1 | 1/2020 | Limb et al. | |
| 2021/0313529 A1* | 10/2021 | Khodagholy | G01N 27/414 |
| 2024/0049994 A1* | 2/2024 | Yin | A61B 10/0064 |
| 2025/0254793 A1 | 8/2025 | Bihar et al. | |

OTHER PUBLICATIONS

International Search Report and Written Opinion received for PCT Patent Application No. PCT/US2023/018150, mailed on Aug. 30, 2023, 13 pages.

Invitation to Pay Additional Fees received for PCT Patent Application No. PCT/US23/018150, mailed on Jun. 13, 2023, 2 pages.

* cited by examiner

FULLY PRINTED SENSOR WITH INTERNAL ION RESERVOIRS

CROSS-REFERENCE TO RELATED APPLICATIONS

The present application is a U.S. National Stage of International Application No. PCT/US2022/034394, filed on Jun. 21, 2022, entitled "Fully Printed Sensor with Internal Ion Reservoirs", which claims priority to and benefit of 1) U.S. Provisional Application No. 63/330,187, filed Apr. 12, 2022, entitled "Inkjet-Printed Gel-Electronics for Biosensing and Electrostimulation, and 2) U.S. Provisional Application No. 63/213,500, filed Jun. 22, 2021, entitled "Fully Printed Organic Electrochemical Transistors with Internal Ion Reservoirs for Detecting Macronutrients in Raw Plant Sap." The entire contents of each of the aforementioned applications are incorporated herein by reference in their entireties.

GOVERNMENT RIGHTS

This invention was made with government support under grant number 1935594 awarded by the National Science Foundation. The government has certain rights in the invention.

BACKGROUND

Macronutrients such as potassium ($K^+$) and calcium ($Ca^{2+}$) are critical for supporting plant growth and development. However, it is challenging to quantify the concentration of these vital nutrients inside of organisms, such as plants or animals, in real-time. For example, existing nutrient detection methods typically require the excavation and transportation of plant samples to off-site laboratories for characterization, which is labor intensive and time consuming. Accordingly, these is a need for improved technology in this area.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY

Disclosed embodiments include a printed electric circuit comprises a printed planar substrate. The printed planar surface comprises one or more traces integrated into the printed planar structure. The one or more traces comprise a hydrophilic additive to create ion reservoirs within an organic semiconductor layer.

Disclosed embodiments also include a method for printing an electric circuit. The method comprises printing onto a substrate a first layer comprising an Ag ink. Additionally, the method comprises printing onto the substrate a second layer comprising an Ag/AgCl ink. Further, the method comprises printing onto the substrate a third layer comprising a PEDOT:PSS ink, wherein the third layer comprise a hydrophilic additive to create ion reservoirs within an organic semiconductor layer. Further still, the method comprises printing onto the substrate a fourth layer comprising dielectric ink.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages will be set forth in the description which follows, and in part will be obvious from the description, or may be learned by the practice of the teachings herein. Features and advantages of the invention may be realized and obtained by means of the instruments and combinations particularly pointed out in the appended claims. Features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features can be obtained, a more particular description of the subject matter briefly described above will be rendered by reference to specific embodiments which are illustrated in the appended drawings. Understanding that these drawings depict only typical embodiments and are not therefore to be considered to be limiting in scope, embodiments will be described and explained with additional specificity and detail through the use of the accompanying drawings described below.

DETAILED DESCRIPTION

Figure 1:
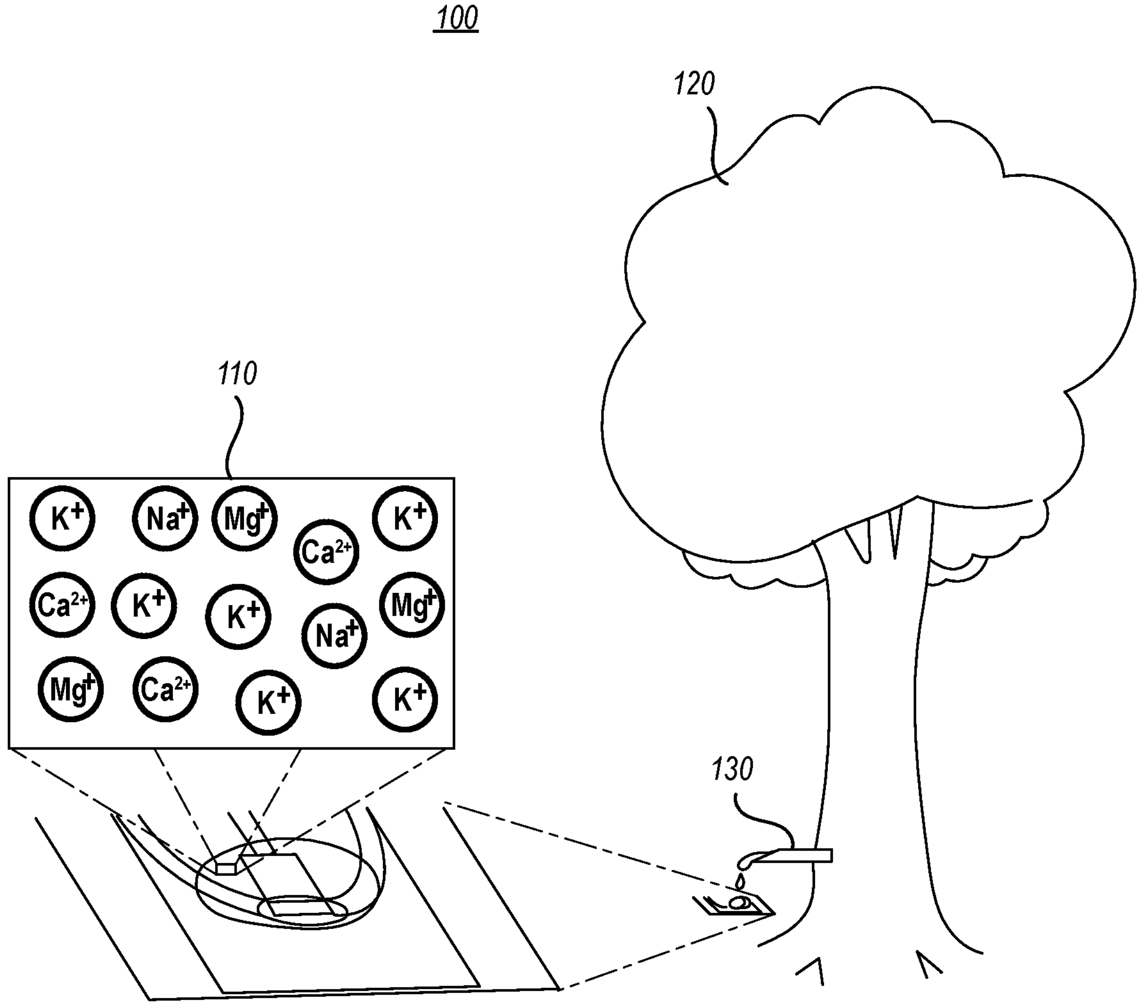
FIG. 1 depicts a schematic diagram of a rapid sap analysis method using an embodiment of a disclosed OECT.

As the effects of climate change lead to more extreme weather, feeding the world's growing population, which is estimated to reach 9.8 billion by 2050, will become increasingly difficult. To secure the global food supply, we must develop new technologies that will improve our farming practices. Consistent plant nutritional and soil testing are proven methods to increase crop yields and provide resiliency amidst fluctuating conditions. Data on the nutrient content in plants allows farmers to make informed fertilization decisions, which improves plant growth, farm efficiency and productivity, and economic output by more than two-fold.

For example, potassium ($K^+$), the most concentrated cationic species in plants, is involved in key physiological processes including the regulation of gas exchange and the movement of water, nutrients, and carbohydrates in plant tissues. Without sufficient amounts of potassium, plant growth becomes stunted, which can result in a major reductions in crop yield. Currently, conventional methods and apparatus fail to quantify the concentration of the potassium ions inside of plants in real-time.

A significant technical shortcoming within conventional nutritional testing methods is that they demand the excavation and transportation of soil and plant tissue samples to off-site laboratories. This testing paradigm requires significant labor, generates chemical waste, and is unable to provide the information that growers need in real-time. In contrast, disclosed embodiments include low-cost bioelectronic sensors that can directly interface with plants. Disclosed embodiments provide an improved technology to monitor crop nutrition and provide farmers with the critical insights to produce healthy yields in a changing climate.

While the examples and disclosures presented herein are focused on interfacing and monitoring plants, one of skill in the art will appreciate that the disclosed technology also includes the ability to interface with and monitor many different reactions. For example, disclosed bioelectronic sensors may be configured to interface with a human brain and provide real-time information of a medical provider. Similarly, bioelectronic sensors may be utilized within livestock to monitor, produce, cheeses, dairy, or any number of different implementations. Accordingly, all descriptions provided herein are merely illustrative and do not limit the invention to usage with plants, unless clearly stated. Additional examples of applications include environmental monitoring (e.g., carbon sequestration, etc.), biomining, monitoring industrial chemical processes, and various other similar processes.

In at least one embodiment, organic electrochemical transistors (OECTs) are used for analyzing plant biological fluids due to their high sensitivity, low voltage, and power requirements, and use of soft materials that are compatible with living tissue. The OECTs can be fabricated using readily scalable additive manufacturing techniques (e.g., inkjet and screen printing) making them suitable for high spatial density in-field measurements that require many sensors to be used. In additional or alternative embodiments, various other types of electronic circuits can be constructed in accordance with embodiments disclosed herein. For example, disclosed embodiments include transistors (includes OECTs, TFTs, OFETs), electrodes, sensors, and capacitors.

Disclosed embodiments include fully printed, mechanically flexible, and ion selective OECTs that can accurately detect macronutrient concentrations in an aqueous solution, such as raw whole plant sap. Additionally, in at least one embodiment, the transconductance of these devices is drastically improved by mixing, or doping, PEDOT:PSS with common sugar alcohols. Such a process may generate "internal ion reservoirs" within the OECT channel. In experimentation, some embodiments of all-printed OECTs show maximum transconductances over 5 mS. By utilizing ion selective membranes (ISMs), OECT-based ion sensors are fabricated that show super-Nernstian sensitivity, selectivity to the target ion against similar ions over five orders of magnitude in concentration, and a limit of detection (LOD) as low as 10 μM. As such, disclosed embodiments provide high-throughput, low-cost, high spatiotemporal assessment of plant nutrition, enabling correlation of sap chemical composition to overall plant and soil health.

Low-cost biosensors that can monitor plant nutritional levels in real-time and be widely distributed over large areas will aid in understanding plant health and improving precision agriculture. Disclosed embodiments include fully printed, mechanically flexible, and ion selective organic electrochemical transistors (OECTs) that can detect macronutrient concentrations in raw whole plant sap. Disclosed embodiments further comprise potassium-selective OECTs, given that potassium is the most concentrated cation in plants and plays a critical role in plant growth and development.

In at least one embodiment, the transconductance of the OECTs is dramatically improved by doping the printable PEDOT:PSS ink with sorbitol to create "internal ion reservoirs" within the channel material. In experiments, the ion sensors demonstrate a high current sensitivity (170 μA $dec^-$), a super-Nernstian sensitivity (99 mV $dec^{-1}$) and low limit of detection (10 μM). Analysis of a raw sap solution using the printed OECTs yielded a determination coefficient of $R^2$=0.985 with respect to the potassium concentrations measured via high pressure liquid ion chromatography (HPLC-IC). Accordingly, disclosed embodiments may be suitable for high-throughput, low-cost plant health monitoring in agricultural and agronomic applications.

Disclosed organic electrochemical transistors (OECTs) are useful devices for analyzing plant biological fluids due to their high sensitivity, low voltage, and power requirements, and use of soft materials that are compatible with living tissues. Additionally, OECTs can be fabricated using readily scalable additive manufacturing techniques (e.g., inkjet and screen printing) making them suitable for high spatial density in-field measurements that require many sensors to be used.

In at least one embodiment, the presence of a charged analyte in solution in contact with the OECT's organic semiconducting channel alters its conductivity, which affects the source-to-drain current ($I_D$). At positive applied gate voltages ($V_G$), cations from the electrolyte are injected into the PEDOT:PSS channel and compensate the negatively charged PSS domains. As a result, the concentration of mobile holes in the PEDOT:PSS film decreases, which decreases the channel conductivity, and thus, the $I_D$ across the channel. The doping/dedoping processes that are responsible for modulating the channel conductivity are based on the volumetric properties of the organic semiconductor, which gives OECT's excellent signal-to-noise ratio compared to other sensing technologies.

While a typical "naked" OECT serves as an excellent ionic activity sensor, it is not able to selectively detect specific ions in a given electrolyte solution. To solve this issue, an ion selective membrane (ISM) layer can be incorporated between the electrolyte and the PEDOT:PSS channel to sense targeted ionic species in the aqueous analyte. By incorporating a polyvinyl chloride (PVC)-based ISM layer between the analyte and the channel, OECTs can be tuned to sense a variety of ions by selectivity dedoping the channel material with the desired (primary) ion.

In an aqueous environment, the ion of interest reversibly binds to the lipophilic ionophore molecule within the membrane. The ionophore compound then acts as an ionic vehicle by transporting the target ion across the membrane material from the analyte solution to the reference solution (or OECT channel). Unfortunately, the PVC matrix of an ISM hinders the transport of ions though the membrane (ionic mobility is ~1000 times lower in an ISM compared to an aqueous solution), which drastically reduces the gate response of OECTs that are directly coupled ISMs. Therefore, in at least one embodiment, the transistor device layers are modified from the ISM to channel in order to directly supply ions to the organic semiconductor and boost device sensitivity. For example, at least one embodiment may comprise a spin-coated polyelectrolyte layer between a microfabricated OECT and ISM that drastically improved the gate response of the device. Additional or alternative embodiments may comprise additives that can dope the raw materials prior to device fabrication. For example, at least one embodiment utilizes sorbitol, which is a biocompatible hydrophilic sugar alcohol that uptakes water molecules. Disclosed embodiments utilize a sorbitol additive to screen printable PEDOT:PSS ink to dramatically boost the gate response and sensitivity of OECT-based ion sensors.

In at least one embodiment, the improved printed OECT device provides a sensing platform that can detect the potassium concentrations from a single drop of raw plant sap in 5 min. Since plants naturally sample and filter soil to produce xylem sap, which is a concentrated solution of relevant analytes and nutrients, it is a useful biological medium to sense for monitoring plant health. As such, disclosed embodiment may provide the fundamental components for a toolkit that can be used by farmers, agronomists, and plant physiologists to understand and correlate the fluctuation in plant sap chemical composition to the overall health of the plant.

Disclosed embodiments may be akin to a "diabetes test strips for plants,' much like the strips that are used to analyze human blood. For example, FIG. 1 depicts a schematic diagram 100 of a rapid sap analysis method using an embodiment of a disclosed OECT 110. In the depicted embodiment of a rapid sap analysis method a small volume of sap is extracted from the living plant 120 and then used by the disclosed device to detect the potassium concentration inside a single drop. The sap may be extracted utilizing a Scholander pressure bomb 130, which is an instrument that is commonly used to measure the water potential of plants. As stated above, the OECTs 110 can be directly coupled to both mammalian and plant systems for in vivo recording from responsive biological environments.

In at least one embodiment, the OECT sensors are fully screen printed and are designed with a planar geometry that included silver source and drain electrodes, silver/silver chloride gates, PEDOT:PSS and polymer blend (PEDOT:PSS combined with sorbitol) channels, and dielectric encapsulants. After annealing the devices, a 100 mM NaCl solution can be drop casted over the channel area to flush out impurities and introduce mobile ions into the channel. A standard PVC-based ISM layer can then be doctor bladed over the channel area to form the potassium-selective OECTs. The devices may be printed in large batches and may be printed on thin polyethylene naphthalate (PEN) substrates, which demonstrated mechanical flexibility and biocompatibility.

In at least one embodiment, the amount of sorbitol added to the PEDOT:PSS ink is below ˜25 wt. %. Otherwise, the viscosity of the ink may become too high to permit consistent, homogenous prints. To assess whether the sorbitol additive boosts printed OECT performance, devices were manufactured that included both 0 wt. % (0-OECTs) and 25 wt. % (25-OECTs) sorbitol added to the PEDOT:PSS channel prior to printing. After device fabrication, the devices were treated with 100 mM NaCl and tested in 60 mM KCl. 60 mM KCl was selected as the standard electrolyte solution because it represents the maximum concentration of potassium ions that are typically measured in plant xylem sap.

Figure 2A:
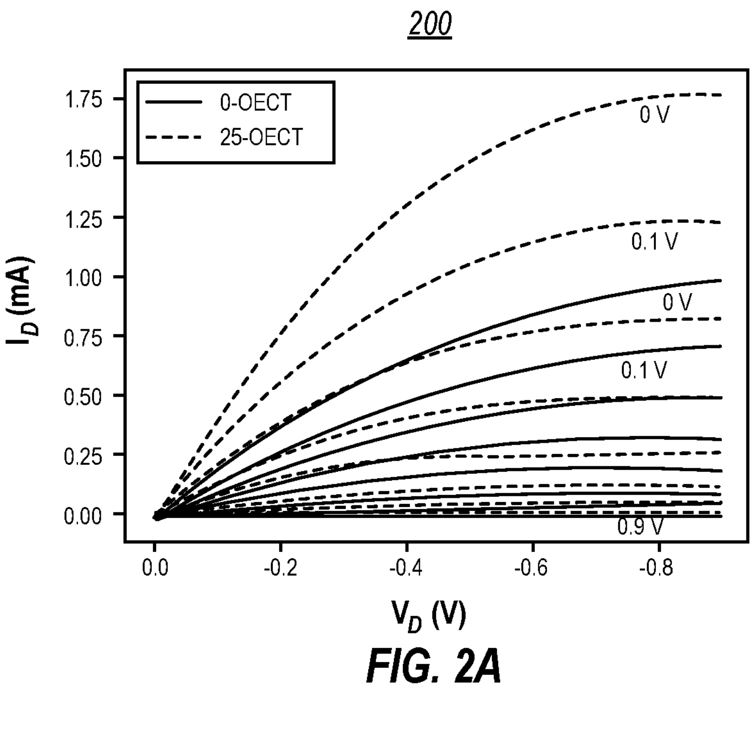
FIG. 2A illustrates charts showing measurements for experiments with embodiments of OECTs.
Figure 2B:
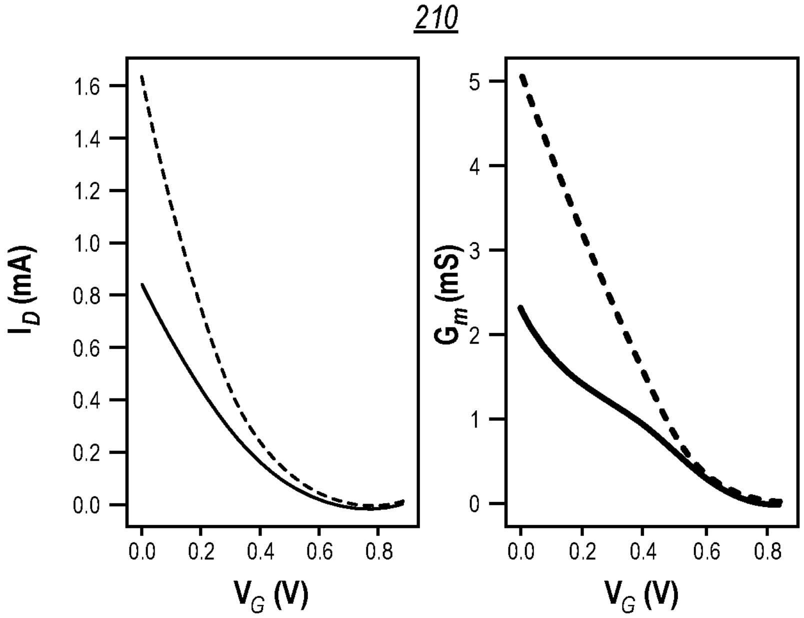
FIG. 2B illustrates charts showing measurements for experiments with embodiments of OECTs.

FIGS. 2A and 2B illustrate charts 200, 210 showing measurements for experiments with embodiments of OECTs. As the output curves show in FIG. 2A, the OECTs were operating in depletion mode (as expected), where the $I_D$ decreases with respect to positive $V_G$ due to the dedoping process. Furthermore, it appears the sorbitol not only increased the conductivity of the OECT channel, but also improved the gate response of the device over a range of applied gate voltages ($0V \leq V_G \leq 0.9V$). The transfer and transconductance characteristics are depicted in FIG. 2B and point to a maximum transconductance ($G_m$) that increases by more than twofold (2.4 to 5.0 mS) from the addition of sorbitol.

The following described mechanism(s) may explain the drastic increase in transconductance for the sorbitol-doped PEDOT:PSS OECTs. First, the sorbitol unscrambles the coiled PEDOT and PSS domains and arranges them into linear chains, which reduces the PEDOT hole hopping distance and enhances film conductivity. Next, the ion treatment step introduces mobile ions into the bulk structure of the film and creates a reservoir of mobile ions within the channel that bind to the sorbitol's alcohol functional groups.

It is worth noting that the sorbitol increases the PEDOT:PSS film thickness by more than twofold from 1 μm to 2.5 μm, which could also attribute to the increase in transconductance. In at least one embodiment, the sorbitol may also increase the porosity of the PEDOT:PSS film, which allows a higher concentration of ions to embed themselves within the film's volume.

By employing PVC-based ISMs doped with potassium ionophores, potassium selective OECTs may be manufactured with both PEDOT:PSS (S-0-OECT) and PEDOT:PSS combined with 25 wt. % sorbitol (S-25-OECT) channels. In at least one embodiment, the S-25-OECT may be associated with a much higher transient gate response compared to the S-0-OECT, which may indicate that the sorbitol is able to capture a much higher concentration of Nations.

In an experiment on an embodiment of an OECT, to extract the steady-state transistor behavior of the potassium-selective OECTs, a gate pulse measurement was conducted by pulsing applied gate voltages in 60 s intervals at a constant drain voltage of −0.6 V. Based on the results, the S-25-OECTs demonstrated a gate response (change in $I_D$) that was more than twofold greater than that of the S-0-OECTs. This result indicates that doping PEDOT:PSS with sorbitol improves not only improves the performance of naked OECTs, but also the performance of OECTs coupled to ISMs.

In at least one embodiment, the S-25-OECT (25 wt. % sorbitol in channel) may have such a drastic increase in gate response because the sorbitol molecules in the channel were able to uptake a much larger concentration of $Na^+$ ions during the NaCl treatment step. After the potassium-ISM is deposited over the channel, the $Na^+$ ions may then be unable to diffuse out of the channel, which serves as a sort of internal supply of ions that can dedope the channel.

In at least one embodiment, the OECT may comprise a much higher $I_D$ response to $K^+$ ions compared to the interfering ions across a large range of concentrations ($10^{-6}$-$10^{-1}$ M). In at least one embodiment, the $K^+$ ion response of the OECT is linear over five orders of magnitude with a current sensitivity of 170 μA $dec^{-1}$ and an estimated limit of detection (LOD) of 10 μM. In experimental data, the LOD was determined by the IUPAC's definition, which is the intersection of the linear portion of the calibration curve and a line crossing the current response at low ion ($K^+$) concentration. Another sensor parameter is based on the membrane potential ($E_m$), which is defined as the boundary potential at the electrolyte-membrane interface of the OECT (assuming the membrane activity remains constant). The $E_m$ for each concentration can be calculated using the Nernstian equation (Equation 1) below, $$E_m = E^0 + \frac{kT}{ne} \ln [M^{n+}] \qquad \text{(Equation 1)}$$

where $E^0$ is the formal potential, $[M^{n+}]$ represents the concentration of the analyte ion, k is the Boltzmann's constant, T is the temperature, n is the valency of the analyte ion and e is the charge of an electron.

A gate pulse measurement was conducted and for the ion selective device in blank solution (DI water) to quantify the device's current response to increasing applied gate voltages. The $E_m$ for each ion concentration was then calculated using this blank transfer curve, which was collected at the same drain voltage ($V_D$=−0.6 V) as the real-time response measurements. The $E_m$ sensitivity showed a super-Nernstian slope of 99 mV $dec^{-1}$.

In the tested embodiment, the selectivity coefficients for each interfering ion were calculated to be $$-\log_{K,Na}^{pot} = 4,\ -\log_{K,Ca}^{pot} = 4.2 \text{ and } -\log_{K,Mg}^{pot} = 4.7$$

using the matched potential method, which takes the ratio of primary to interfering ion activity (concentration) that results in the same potential change. Each of the calculated coefficients falls into the expected range of values for ion sensors that employ ISMs with similar compositions.

Various embodiments of ion selective OECTs were tested to detect the potassium concentrations in five different raw sap solutions. A Scholander presume bomb was used to extract the xylem fluid from four different plant species: *Zea, Maize, Prunus* and *Picea*. The Maple sap solution was produced by simply diluting pure maple syrup, which is concentrated sap tapped from a maple tree. For each sap solution, a small volume was drop casted over the S-25-OECT's active areas and constant voltages ($V_D$=−0.6 V and $V_G$=0.1 V) were applied to the device terminals to stabilize the device.

After 5 min (300 s), the equilibrated drain current, $I_D$ was measured for each sap solution and DI water with respect to time for 1 min. Note that DI water was also tested to serve as a reference current for a blank solution. To determine the potassium content from the S-25-OECT, another calibration curve was collected that focused on the concentration range of potassium (1-60 mM) that we expect to detect in plant sap based on the literature. The current response (ΔI) for each sap solution was calculated by taking the difference between the steady state $I_D$ values of the device in DI water and the respective sap solution. The true potassium concentration for each sap solution was gathered using ion chromatography (IC). The OECT predicted concentration based on the OECT response was then compared to the true concentration for each sap solution. Based on the results, the average error of this tested embodiment for detecting the true concentration of potassium in a plant sap solution is in the range for most potassium human blood tests making this viable method for in vitro testing.

Accordingly, doped PEDOT:PSS ink with sorbitol can be used to create OECT channels with internal ion reservoirs, which leads to a drastic improvement in device performance. The all-printed OECTs demonstrated maximum transconductances over 5 mS. Furthermore, disclosed embodiments utilize ion selective membranes (ISMs) to develop OECT-based ion sensors that have super-Nernstian sensitivity, high selectivity, and low limit of detection. Further, disclosed embodiments provide a highly sensitive, sensing platform to accurately extract the potassium ion concentrations in several raw whole plant saps. Based on the accuracy of various experimental results, disclosed embodiments provide a potential path to high-throughput, low-cost, high spatiotemporal assessment of plant nutrition, enabling correlation of sap chemical composition to overall plant and soil health.

In at least one embodiment, the organic semiconducting channel material is prepared by mixing the PEDOT:PSS ink for 2 hours at 1200 RPM using Southwest's Digital Overhead Stirrer. For the polymer blend (PEDOT:PSS plus sorbitol) mixture, 30 g of PEDOT:PSS may be combined with 25 wt. % sorbitol and mixed for 20 minutes. The ISM solution may be formed by mixing high molecular weight PVC (33 wt. %), plasticizer (2-NPOE, 65 wt. %), cation exchanger ($KT_4ClPB$, 0.2 wt %) and the potassium ionophore III (2 wt. %) in THF (300 mg/4 mL). The THF solvent may be used to homogenize the membrane components and achieve an ideal membrane viscosity for deposition.

Figure 3:
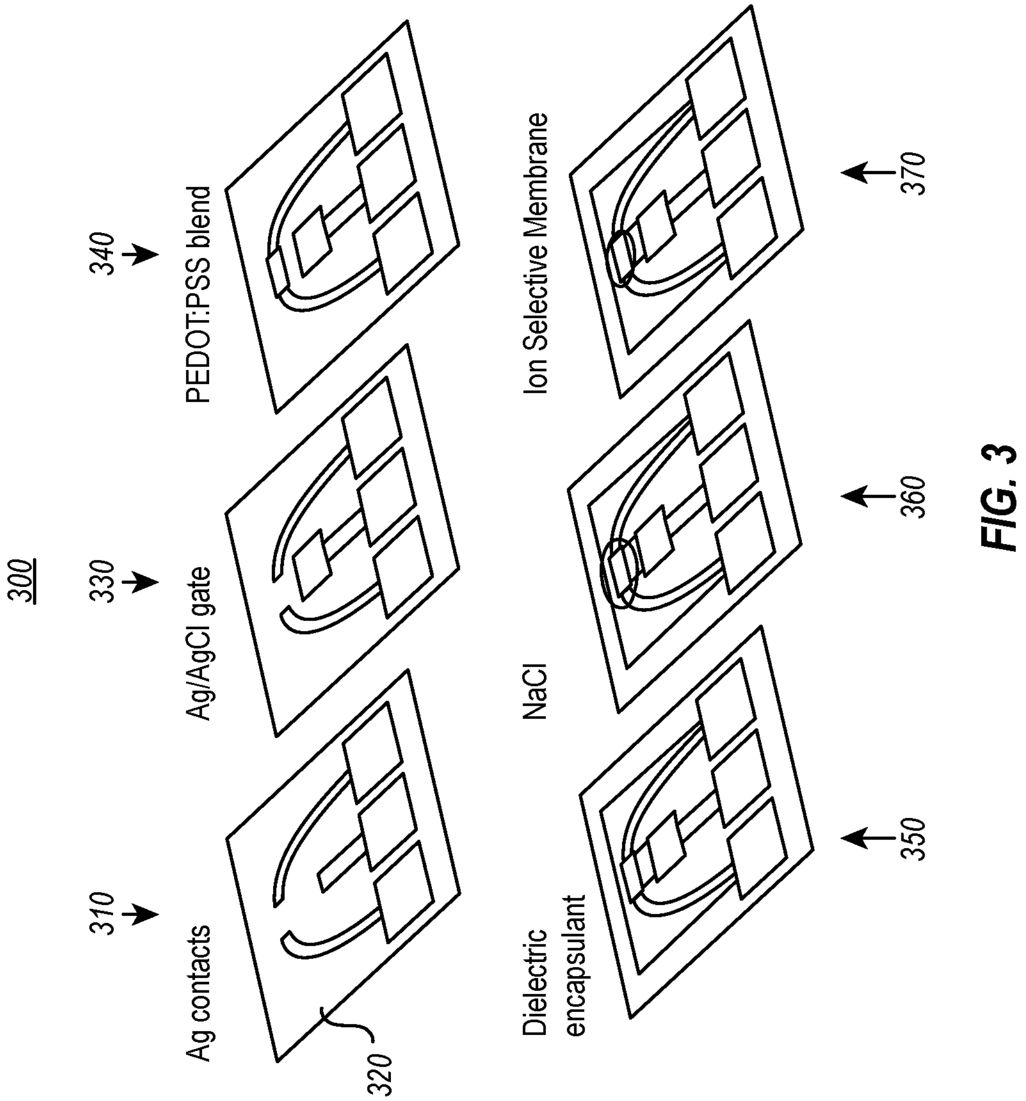
FIG. 3 illustrates an overview of an OECT manufacturing process.

In at least one embodiment, the OECT devices are manufactured with a screen-printing process. Prior to device fabrication, the PEN substrates may be sonicated for 15 min in acetone, sonicated for 15 min in isopropanol and dried with a stream of nitrogen ($N_2$) gas. Next, four layers may be printed to form the device array. FIG. 3 illustrates an overview of an OECT manufacturing process 300. As depicted, the first layer 310, which served at the source and drain electrodes, may be printed on a substrate 320 with the Ag ink and cured at 130° C. for 30 min. The first layer 310 may comprise a final dry thickness of ~20 μm. The second layer 330, which formed the gate electrode, may be printed with the Ag/AgCl ink and cured at 130° C. for 30 min. The second layer 330 may comprise a dry thickness of ~25 μm thick. The third layer 340, which served as the organic semiconducting channel, may be printed with the plain PEDOT:PSS or the polymer blend and annealed at 120° C. for 20 min. The third layer 340 may comprise a final thickness of ~1 μm and ~2.5 μm, respectively. The fourth layer 350 was printed with the dielectric ink and annealed at 120° C. for 30 min. The fourth layer 350 may comprise a dry thickness of ~30 μm. Additionally, the fourth layer 350 may encapsulate all device surfaces except the gate, channel, and contact pad areas. The exposed gate area may comprise 2 $mm^2$ and the exposed channel area may comprise 0.5 $mm^2$.

In at least one embodiment, after printing the final layer (dielectric), the OECTs were immersed in a 100 mM NaCl solution 360 for 1 hour to allow the sorbitol to soak up the $Na^+$ ions potentially creating an "internal ion reservoir" within the channel. The OECTs may be rinsed with DI water prior to functionalization. The patterned stencil may then be taped over the substrate exposing only the channel area. 50 μL of the ISM solution 370 may then be drop casted across one edge of the stencil material next to the exposed device channel area. The ISM solution may then be uniformly deposited through the patterned stencils and over the channel area using Zehntner's ZUA 2000 blade coating system (speed dial set to 40). The final thickness of the ISM film may be ~15 μm.

For the sake of example and explanation, the above disclosure discussed OECTs and the use of a sorbitol additive. However, various additional or alternative embodiments may also be utilized. For example, in at least one embodiment, different materials may be added to conjugated polymers before printing film to form OECT device with composite channel material. Additionally, a variety of different printing techniques may be utilized, including but not limited to, doctor blading, screen printing, inkjet printing, slot die coating, FDM printing, SLA printing, etc. Additionally, in at least one embodiments various different substrate materials may be utilized. Exemplary substrate materials may one or more of the following: PEN, PET, polyester, polystyrene, wood, hydrogels, sponges, animal skin, plant tissue (e.g., stems, leaves, etc.), tattoo paper, glass, textiles, and various other substrates that can be printed upon.

In at least some embodiments, a variety of different channel materials may also be utilized. For example, channel materials may comprise both p-type and n-type material. Conventionally, OECTs are based on p-type polymers (e.g., PEDOT:PSS); however, new types of material that can be doped with electrons (i.e., n-type doped). In at least one embodiment, a P-type material may comprise one or more of the following: PEDOT:PEG, polypyrol, poly(3,4-ethylenedioxythiophene) (PEDOT), polyaniline (PANT), polypyrrole (PPy), poly(phenylene vinylene) (PPV), poly(arylene), polyspirobifluorene, poly(3-hexylthiophene) (P3HT), poly (o-methoxyaniline) (POMA), poly(o-phenylenediamine) (PPD), or poly(p-phenylene sulfide). The conductive polymers can also include functionalized PEDOT with additional functional groups on the end of the polymer chain (e.g., PEDOT-TMA (PTMA), PEDOT-PEG, and PEDOT block PEG). In at least one embodiment, a N-type material may comprise one or more of the following: naphthalene diimide (NDI) polymers, BBL, PNBSF, PNDIV-BT, PNDOF-T2, P4, TEG-N2200, etc.

Additionally or alternatively, in at least one embodiment, the doping material may comprise a hydrophilic additive. For example, the hydrophilic additive may comprise sorbitol, or some sugar alcohol (e.g., mannitol, xylitol, glycerol, lactitol, erythritol, isomalt, maltitol, arabitol, hydrogenated starch hydrolysates (HSH)). Additionally or alternatively, the hydrophilic additive may comprise methyl cellulose, hydroxyethyl cellulose, sucrose, fructose, lactose, carboxymethylcellulose, or carboxymethylchitosan. Disclosed embodiments of the hydrophilic additive can further comprise polymer additives that can absorb ions or create hydrogel network within PEDOT:PSSS structure. Example of polymer additives include acrylates, sodium polyacrylate (called "WaterLock" commercially), acrylamides, polyvinyl alcohol (PVA), and poly(ethylene glycol) diacrylate (PEGDA)). Further examples of hydrophilic additive include polyelectrolytes (e.g., ion exchange resins) and inorganic particles (e.g., porous metal oxides).

Accordingly, disclosed embodiments include a variety of different hydrophilic additives, substrates, and manufacturing techniques. Additionally disclosed embodiments demonstrate improved device transconductance (dI/dVg) and improved ion sensor sensitivity in OECTs.

Additionally or alternatively, disclosed embodiments may be utilized for detecting ions in a variety of different aqueous solutions, including raw (whole) biological fluids. For example, disclosed embodiments may be utilized for detecting ions within human and animal blood, sweat, saliva, tears, and other bodily fluids. Such detections may be utilized for tracking brain activity or other health metrics, such as diabetes. Similarly, disclosed embodiments may be utilized for detecting ions in plant sap or in hydroponic solutions (e.g., aquaponics, aeroponics, and aquaculture).

Additionally, disclosed apparatus, systems and methods can be utilized within a variety of different fully integrated system for large scale sensing applications based on OECTs. In various embodiments, the device may be in communication with a source measurement unit (SMU), an RFID chip, a LoRA communication device, a WiFi device, a Bluetooth device, or any number of other devices for communication information. As such, a user may be able to gather information from multiple disclosed devices wirelessly or through wired communication. Additionally, devices may be associated with GPS devices, RF triangulation device, ultra-wide band circuits, or other devices for localization purposes.

Disclosed embodiments may be utilized in procession agriculture, such as wine vineyards, crop yields (e.g., corn, potatoes, other produce), hemp, and other related agricultural products. Similarly, disclosed embodiments may be utilized in golf courses, home/commercial gardens, environmental monitoring (carbon sequestration, etc.), bioremediation, biomining, and various human/animal health applications.

Figure 4:
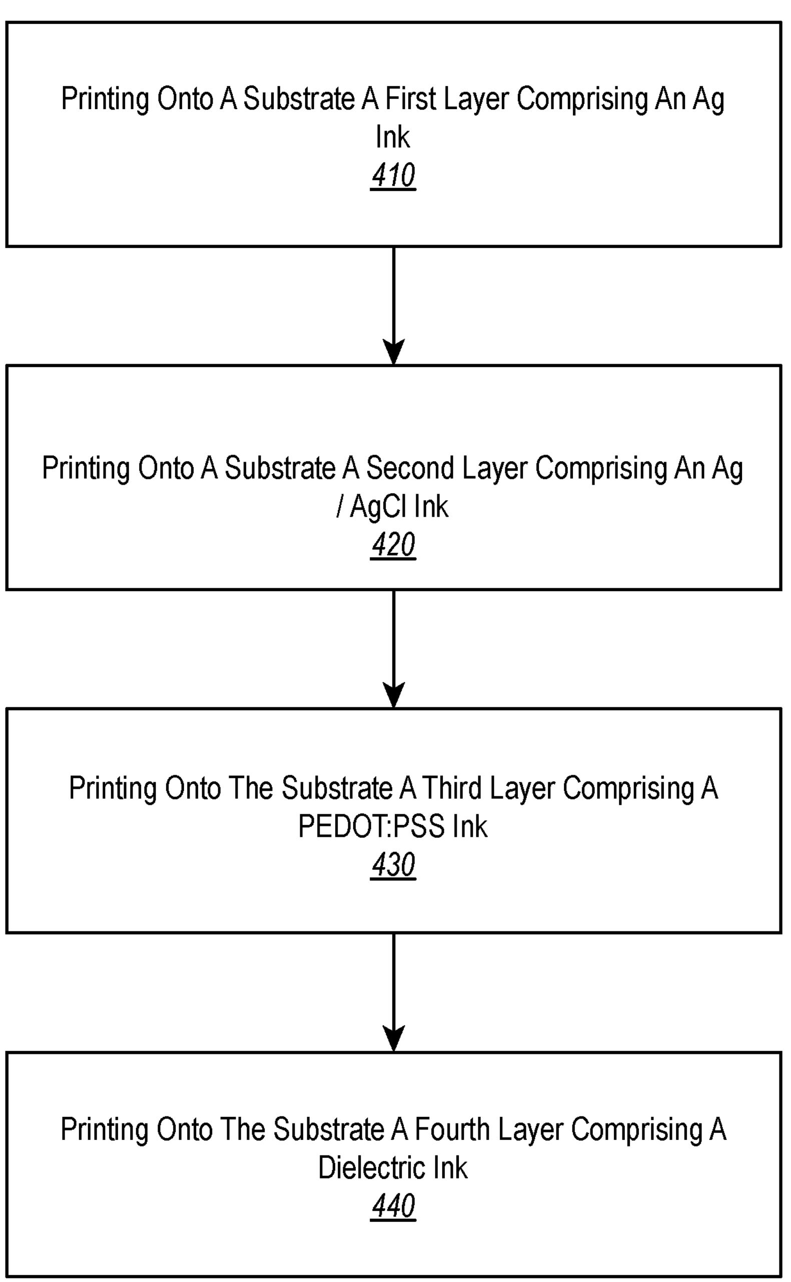
FIG. 4 depicts a flowchart of steps in an embodiment of a method 400 for printing an electric circuit.

FIG. 4 depicts a flowchart of steps in an embodiment of a method 400 for printing an electric circuit. Method 400 comprises a step 410 of printing onto a substrate a first layer comprising an Ag ink. For example, as depicted and described with respect to FIG. 3, a first layer 310, comprising Ag contacts, is printed on a substrate 320. The substrate, ink, and printing methods may comprise a variety of different methods and substances as disclosed herein.

Method 400 also comprises a step 420 of printing onto the substrate a second layer comprising an Ag/AgCl ink. For example, as depicted and described with respect to FIG. 3, a second layer 330, comprising an Ag/AgCl gate, is printed on a substrate 320. The substrate, ink, and printing methods may comprise a variety of different methods and substances as disclosed herein.

Additionally, method 400 comprises a step 430 of printing onto the substrate a third layer comprising a PEDOT:PSS ink, wherein the third layer comprise a hydrophilic additive to create ion reservoirs within an organic semiconductor layer. For example, as depicted and described with respect to FIG. 3, a third layer 340, comprising an PEDOT:PSS ink, is printed on a substrate 320. The PEDOT:PSS ink may comprise a hydrophilic additive, such as sorbitol sugar. The substrate, ink, and printing methods may comprise a variety of different methods and substances as disclosed herein.

Further, method 400 comprises a step 440 of printing onto the substrate a fourth layer comprising dielectric ink. For example, as depicted and described with respect to FIG. 3, a fourth layer 350, comprising a dielectric encapsulant, is printed on a substrate 320. The fourth layer may encapsulate all device surfaces except the gate, channel, and contact pad areas. The substrate, ink, and printing methods may comprise a variety of different methods and substances as disclosed herein.

The present invention is further specified in the following clauses.

Clause 1: A printed electric circuit, the printed electric circuit comprising: a printed planar substrate, the printed planar surface comprising one or more traces integrated into the printed planar structure; wherein the one or more traces comprise a hydrophilic additive to create ion reservoirs within an organic semiconductor layer.

Clause 2: The printed electric circuit as recited in Aspect 1, further comprising: one or more contact pads configured to communicate with a source measure unit (SMU).

Clause 3: The printed electric circuit as recited in any of the preceding clauses, wherein the hydrophilic additive comprises a sugar alcohol additive.

Clause 4: The printed electric circuit as recited in any of the preceding clauses, wherein the sugar alcohol additive comprises a sugar alcohol additive comprises sorbitol.

Clause 5: The printed electric circuit as recited in any of the preceding clauses, wherein the additive is mixed with a PEDOT:PSS ink.

Clause 6: The printed electric circuit as recited in any of the preceding clauses, wherein the sugar alcohol additive comprises at least one of the following: mannitol, xylitol, glycerol, lactitol, erythritol, isomalt, maltitol, arabitol, and hydrogenated starch hydrolysates (HSH).

Clause 7: The printed electric circuit as recited in any of the preceding clauses, wherein the hydrophilic additive comprises at least one of the following: methyl cellulose, hydroxyethyl cellulose, sucrose, fructose, lactose, carboxymethylcellulose, carboxymethylchitosan.

Clause 8: The printed electric circuit as recited in any of the preceding clauses, wherein the printed electric circuit comprises an ion selective organic electrochemical transistor (OECT).

Clause 9: The printed electric circuit as recited in any of the preceding clauses, wherein the OECT comprises: a first layer comprising an Ag ink, a second layer comprising an Ag/AgCl ink, a third layer comprising a PEDOT:PSS ink; and a fourth layer comprising dielectric ink.

Clause 10: The printed electric circuit as recited in any of the preceding clauses, wherein the printed electric circuit comprises one or more of the following: a transistor, an electrode, a sensor, or a capacitor.

Clause 11: The printed electric circuit as recited in any of the preceding clauses, further comprising an ion selective membrane.

Clause 12: The printed electric circuit as recited in any of the preceding clauses, wherein the ion selective membrane comprises a potassium ionophore.

Clause 13: A method for printing an electric circuit, the method comprising: printing onto a substrate a first layer comprising an Ag ink, printing onto the substrate a second layer comprising an Ag/AgCl ink, printing onto the substrate a third layer comprising a PEDOT:PSS ink, wherein the third layer comprise a hydrophilic additive to create ion reservoirs within an organic semiconductor layer; and printing onto the substrate a fourth layer comprising dielectric ink.

Clause 14: The method as recited in clause 13, wherein the hydrophilic additive comprises a sugar alcohol.

Clause 15: The method as recited in either of clauses 13 or 14, further comprising: placing an ion selective membrane onto the fourth layer.

The present invention may be embodied in other specific forms without departing from its spirit or characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A printed electric circuit, the printed electric circuit comprising:

a printed planar substrate, the printed planar substrate comprising one or more traces integrated into the printed electric circuit;

wherein the one or more traces comprise a hydrophilic additive to create ion reservoirs within an organic semiconductor layer; and a printed PEDOT:PSS ink layer forming the organic semiconductor layer, wherein the printed PEDOT:PSS ink layer has a thickness between 1 μm and 2.5 μm.

2. The printed electric circuit as recited in claim 1, further comprising:

one or more contact pads configured to communicate with a source measure unit (SMU).

3. The printed electric circuit as recited in claim 1, wherein the hydrophilic additive comprises a sugar alcohol additive.

4. The printed electric circuit as recited in claim 3, wherein the sugar alcohol additive comprises sorbitol.

5. The printed electric circuit as recited in claim 3, wherein the sugar alcohol additive is mixed with the PEDOT:PSS ink layer.

6. The printed electric circuit as recited in claim 3, wherein the sugar alcohol additive comprises at least one of the following: mannitol, xylitol, glycerol, lactitol, erythritol, isomalt, maltitol, arabitol, and hydrogenated starch hydrolysates (HSH).

7. The printed electric circuit as recited in claim 1, wherein the hydrophilic additive further comprises at least one of the following: methyl cellulose, hydroxyethyl cellulose, sucrose, fructose, lactose, carboxymethylcellulose, carboxymethylchitosan.

8. The printed electric circuit as recited in claim 1, wherein the printed electric circuit further comprises an ion selective organic electrochemical transistor (OECT).

9. The printed electric circuit as recited in claim 8, wherein the OECT comprises:

a first layer comprising an Ag ink, a second layer comprising an Ag/AgCl ink, a third layer comprising a PEDOT:PSS ink, and a fourth layer comprising dielectric ink.

10. The printed electric circuit as recited in claim 1, wherein the printed electric circuit further comprises one or more of the following: a transistor, an electrode, a sensor, or a capacitor.

11. The printed electric circuit as recited in claim 1, further comprising an ion selective membrane.

12. The printed electric circuit as recited in claim 11, wherein the ion selective membrane comprises a potassium ionophore.

13. A method for printing an electric circuit, the method comprising:

printing onto a substrate a first layer comprising an Ag ink, printing onto the substrate a second layer comprising an Ag/AgCl ink, printing onto the substrate a third layer comprising a PEDOT:PSS ink, wherein the third layer further comprises a hydrophilic additive to create ion reservoirs within the third layer, wherein printing the third layer comprises forming an organic semiconducting channel with a thickness between 1 μm and 2.5 μm, and printing onto the substrate a fourth layer comprising dielectric ink.

14. The method as recited in claim 13, wherein the hydrophilic additive comprises a sugar alcohol.

15. The method as recited in claim 13, further comprising:

placing an ion selective membrane onto the fourth layer.

* * * * *